United States Patent [19]

Ito et al.

[11] 4,314,845

[45] Feb. 9, 1982

[54] N⁴-PHENOXYALKANOYLSULFANILA-MIDES AND HERBICIDAL COMPOSITION CONTAINING THE SAME

[75] Inventors: Kanji Ito, Hirakata; Kenji Ikawa, Osaka; Hisajiro Yukinaga, Kusatsu; Jitsuo Sugita, Ikeda, all of Japan

[73] Assignee: Shionogi & Co., Ltd., Osaka, Japan

[21] Appl. No.: 185,965

[22] Filed: Sep. 9, 1980

[30] Foreign Application Priority Data

Sep. 21, 1979 [JP] Japan ................... 54-122423

[51] Int. Cl.³ ................... A01N 37/24; C07C 103/22
[52] U.S. Cl. ................... 71/103; 71/76; 260/397.7 R
[58] Field of Search ................... 71/103, 76; 260/397.7 R

[56] References Cited

U.S. PATENT DOCUMENTS 3,849,110 11/1974 Soper et al. ................... 71/103
4,070,176 1/1978 Oshio et al. ................... 71/103 OR
4,113,463 9/1978 Oshio et al. ................... 260/297.6 R X

FOREIGN PATENT DOCUMENTS 4316 9/1966 France.

OTHER PUBLICATIONS

Ariesan et al., Chem. Abst., 84:116338e (1976).
Northey, The Sulfonamides and Allied Compounds, pp. 150 to 152, 209–228, Reinhold Publishing Corp. NY (1948).
Jahan et al., Chemical Abstracts, vol. 91, abst. 74317j (1979).
Krewson et al., J. Agr. Food Chem., vol. 7, pp. 118–122 (1959).

Primary Examiner—John D. Randolph
Attorney, Agent, or Firm—Birch, Stewart, Kolasch and Birch

[57] ABSTRACT

$N^4$-Phenoxyalkanoylsulfanilamides of the formula:

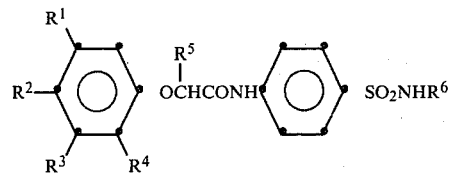

(wherein $R^1$, $R^2$, $R^3$ and $R^4$ each independently represents hydrogen, halogen, nitro or lower alkyl, $R^5$ represents hydrogen or lower alkyl, and $R^6$ represents hydrogen, lower alkoxycarbonyl, lower alkanoyl or carbamoyl) and alkali metal or alkaline earth metal salt thereof, and a herbicidal composition containing at least one of said $N^4$-phenoxyalkanoylsulfanilamides are disclosed.

24 Claims, No Drawings

N[4]-PHENOXYALKANOYLSULFANILAMIDES AND HERBICIDAL COMPOSITION CONTAINING THE SAME

BACKGROUND OF THE INVENTION

1. Field of the Invention

The present invention relates to novel N[4]-phenoxyalkanoylsulfanilamides and herbicidal composition containing at least one of said compounds in an amount sufficient for exhibiting the herbicidal activity. More particularly, it is concerned with N[4]-phenoxyalkanoylsulfanilamides of the formula:

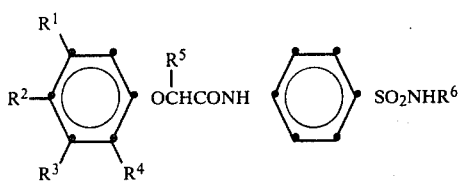

(wherein $R^1$, $R^2$, $R^3$ and $R^4$ each independently represents hydrogen, halogen, nitro or lower alkyl, $R^5$ represents hydrogen or lower alkyl, and $R^6$ represents hydrogen, lower alkoxycarbonyl, lower alkanoyl or carbamoyl) and alkali metal or alkaline earth metal salts thereof, and herbicidal compositions containing at least one of said N[4]-phenoxyalkanoylsulfanilamides.

In the definition of the above formula (I), the terms herein used are illustrated as follows:

Lower alkyl means $C_1$–$C_5$ alkyl such as methyl, ethyl, propyl, isopropyl, butyl, isobutyl, t-butyl, pentyl, isopentyl and sec-pentyl, lower alkoxycarbonyl means $C_2$–$C_6$ alkoxycarbonyl such as methoxycarbonyl, ethoxycarbonyl, propoxycarbonyl, butoxycarbonyl and pentyloxycarbonyl, lower alkanoyl means $C_1$–$C_5$ alkanoyl such as formyl, acetyl, propionyl, butyryl and valeryl, halogen means chlorine, iodine, bromine and fluorine, alkali metal means lithium, sodium and potassium; and alkaline earth metal means magnesium, calcium and barium.

The most preferred compounds among the above include those having the formula:

(wherein $R^1$, $R^2$, $R^3$, $R^4$ and $R^5$ each has the same significance as defined above) and sodium or potassium salts thereof, from a practical point of view which will be discussed later.

DESCRIPTION OF THE PRIOR ART

Phenoxyalkanoic acids, and salts, esters or other derivatives thereof, have widely been known to have hormonal activities promoting or inhibiting the growth of plants. On the other hand, N[1]-alkanoylsulfanilamides and N[1]-alkanoylsulfanilureas have been known to have non-hormonal herbicidal activities (British Pat. No. 1,040,541).

The compounds of the present invention have the same moiety as the aforementioned known herbicides. However, the activities of the new compounds are distinctively different from those of the known compounds. In addition, the herbicidal activities of the compounds of the present invention are unexpectedly potent and more unique than those expected from simple combinations of the known structurally correlated compounds.

These facts are confirmed by the results of experiments which will be described in detail later.

SUMMARY OF THE INVENTION

It is therefore the primary object of the present invention to provide novel compounds (I) defined in the beginning of the specification and claimed in the present application.

It is another object of the present invention to provide herbicidal compositions containing at least one of the above-indicated compounds (I) as active ingredients.

A further object of the present invention is to provide a process for preparing the novel compounds (I).

DESCRIPTION OF THE PREFERRED EMBODIMENTS

According to one aspect of the present invention, the compounds (I) can be obtained by contacting the starting compounds of the formula:

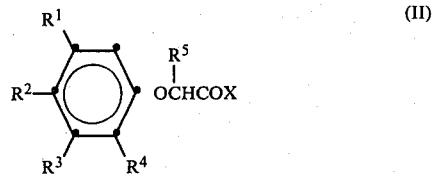

(wherein $R^1$, $R^2$, $R^3$, $R^4$ and $R^5$ each has the same significance as defined above, and X represents a hydroxy, halogen or lower alkoxy) with sulfanilamides of the formula:

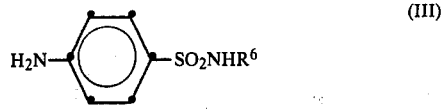

(wherein $R^6$ has the same significance as defined above), if necessary, in the presence of an organic or inorganic base or a dehydrating agent, and an inert solvent.

The starting compounds of the formula (II) can be exemplified as free acid, halides (e.g., chloride, bromide and iodide) or lower alkyl esters (e.g., methyl ester, ethyl ester and propyl ester) of phenoxyacetic acids such as, 4-chlorophenoxyacetic acid, 4-fluorophenoxyacetic acid, 4-bromophenoxyacetic acid, 2-chloro phenoxyacetic acid, 3-chlorophenoxyacetic acid, 2,4-dichlorophenoxyacetic acid, 3,4-dichlorophenoxyacetic acid, 2,4,5-trichlorophenoxyacetic acid, 2-methyl-4-chlorophenoxyacetic acid, 3-methylphenoxyacetic acid, 4-methylphenoxyacetic acid, 3,5-dimethylphenoxyacetic acid, 3-nitrophenoxyacetic acid, 4-nitrophenoxyacetic acid, 2,4-dinitrophenoxyacetic acid, 1-(2-methyl-4-chlorophenoxy)propionic acid, and the like.

The sulfanilamides of the formula (III) can be exemplified by, sulfanilamide, N[1]-methoxycarbonyl-sulfanilamide, N[1]-acetylsulfanilamide, N[1]-carbamoylsulfanilamide and the like.

The organic base includes pyridine, triethylamine or the like. The inorganic base can be exemplified by sodium hydride, potassium hydride, sodium hydroxide, patassium hydroxide, sodium amide, sodium alkoxide or the like. The dehydrating agent includes dicyclohexyl-carbodiimide (DCC).

Said inert organic solvent can be exemplified by benzene, toluene, dioxane, tetrahydrofuran, diethyl ether, pyridine, dimethylformamide, dimethylsulfoxide or the like. It is convenient for simplifying the manufacturing process to use a solvent such as pyridine which also serves as said base.

The reaction generally proceeds at a temperature ranging from room temperature to the boiling point of the solvent used. Alternatively, the reaction may be carried out under fused conditions at an elevated temperature without using any solvent when the starting compound (II) is used as free acid or ester; in such a case, the reaction is conducted in an inert atmosphere (e.g., nitrogen or argon atmosphere) or under reduced pressure.

Thus obtained compounds (I) may further be converted into an $N^1$-salt of alkali metal or alkaline earth metal by simply treating the compounds with alkali metal hydroxides or alkaline earth metal hydroxides. Moreover, the compound (I) may be converted into an ammonium salt in a conventional manner. Representative of the compounds (I) are exemplified in Table 1 below.

TABLE 1

$$R^2 - \underset{R^3}{\underset{|}{\overset{R^1}{\overset{|}{\bigcirc}}}} - \overset{R^5}{\underset{|}{O CHCONH}} - \bigcirc - SO_2NHR^6$$

| Compound No. | $R^1$ | $R^2$ | $R^3$ | $R^4$ | $R^5$ | $R^6$ | Melting point (°C.) |
|---|---|---|---|---|---|---|---|
| 1 | H | Cl | H | $CH_3$ | H | H | 218–220 |
| 2 | H | H | H | H | H | $COOCH_3$ | 189–192 |
| 3 | H | Cl | H | H | H | $COOCH_3$ | 246–249 |
| 4 | H | Cl | Cl | H | H | $COOCH_3$ | 196–199 |
| 5 | H | Cl | H | Cl | H | $COOCH_3$ | 198–200 |
| 6 | H | Cl | H | $CH_3$ | H | $COOCH_3$ | 184–185 |
| 7 | ($N^1$-sodium salt of the compound No. 6) | | | | | | 243–244 |
| 8 | ($N^1$-potassium salt of the compound No. 6) | | | | | | 253 |
| 9 | H | Cl | H | $CH_3$ | H | $CONH_2$ | 198–200 |
| 10 | H | F | H | H | H | $COOCH_3$ | 187–189 |
| 11 | H | Br | H | H | H | $COOCH_3$ | 208–210 |
| 12 | H | $CH_3$ | H | H | H | $COOCH_3$ | 183–185 |
| 13 | H | H | Cl | H | H | $COOCH_3$ | 179–181 |
| 14 | H | H | H | Cl | H | $COOCH_3$ | 197–199 |
| 15 | H | H | $CH_3$ | H | H | $COOCH_3$ | 186–188 |
| 16 | H | H | H | $CH_3$ | H | $COOCH_3$ | 190–191 |
| 17 | H | Cl | H | $CH_3$ | $CH_3$ | $COOCH_3$ | 86–87 |
| 18 | H | Cl | H | $CH_3$ | H | $COCH_3$ | 253–255 |
| 19 | Cl | H | Cl | H | H | $COOCH_3$ | 192–194 |
| 20 | $CH_3$ | H | $CH_3$ | H | H | $COOCH_3$ | 187–188 |
| 21 | H | $NO_2$ | H | H | H | $COOCH_3$ | 183–185 |
| 22 | H | H | $NO_2$ | H | H | $COOCH_3$ | 188–190 |
| 23 | H | $NO_2$ | H | $NO_2$ | H | $COOCH_3$ | 204–206 |

In another aspect of the present invention, there is provided a herbicidal composition containing at least one of said compounds of the formula (I).

In preparing such herbicidal compositions, the compounds (I) are usually diluted with a compatible liquid or solid carrier, being inert to these compounds, to form a formulation convenient for application, for instance, emulsion, dust, wettable powder or granules in combination with suitable and compatible auxiliary agents such as a surfactant, sticking agent and extender, as required.

The herbicidal composition may be applied in amounts ranging from 1.0 to 20.0 grams of the active ingredient per are, but this range is variable in compliance with situations and conditions at the intended application.

If further required, any compatible active ingredient in addition to the compounds (I) may be incorporated into the composition in association with any wetting, dispersing or emulsifying agent.

The liquid carrier or diluent used in the herbicidal composition of the present invention includes water, animal or vegetable oil, a variety of organic solvents which may be exemplified by hydrocarbons, e.g., keroseine, benzene and xylene; halogenohydrocarbons, e.g., chlorobenzene and dichloroethylene; alcohols; and ketones, e.g., acetone and methyl ethyl ketone. The solid carrier includes bentonite, kaolin, clay, talc, acidic terra alba, diatomaceous earth, silicates, fine powdery silica, calcium carbonate and the like.

The surfactants which can be incorporated into the herbicidal preparation may be exemplified as salts of alkylbenzenesulfonic acid, ligninsulfonic acid or dialkylsulfonyl succinic acid; sulfates of higher alcohols, esters of polyoxyethylene sorbitan fatty acid, alkyltrimethylammonium chloride and the like.

The herbicidal activities of the compounds of the present invention are not only higher than those of known herbicides but also very unique in their properties. Namely, these compounds usually act on seeds of noxious weeds to strongly inhibit the emergence but do not affect the growth of the growing weeds or the useful crop after germination as far as applications on upland crop are concerned.

This very fact is significant in that the compounds of the present invention are of high safety to the seeds of useful crops which usually germinate in different depths in the soil. Thus, the compounds can selectively inhibit the emergence of weeds by applying the herbicidal composition to the soil before the transplanting of useful crops.

Substitution of $N^1$-hydrogen with an alkali metal or an alkaline earth metal improves the solubility of the compound (I) in water to enhance the herbicidal activity.

As previously indicated, the compounds of the present invention not only show a potent herbicidal activity in a relatively low dosage level with the least adverse influence on useful crops, but are also very convenient in practical application.

In this way, the compounds of the present invention are applicable at the user's will, as a total herbicide for fallow or uncultivated land and as a selective herbicide for land for agriculture, horticulture or silviculture after seeding, or before or after the transplanting of useful crops.

Accordingly, in the practical application with the compounds of the present invention, a selection of the most suitable compound and/or combination of the selected compounds or that with one or more compatible diluents or carriers should be made in consonance with the particular purpose and requirements in the application.

The requirement will be determined by the species of the weed to be removed, the conditions of the soil whether it may be upland or paddy and its extent of cultivation, and the growth period and transplanting of the useful crops.

In the following description, the present invention will be elucidated in more detail in turn, on the embodiments of synthesis of the compounds, formulation of the herbicidal compositions and application with such compositions.

SYNTHESIS 1

$N^1$-Methoxycarbonylsulfanilamide (7.8 Kg) is dissolved in pyridine (50 L, heated at 45° C.) and cooled down to about 10° C. To this solution is, added 2-methyl-4-chlorophenoxyacetic chloride (7.8 Kg, 1.05 equimolar to the sulfanilamide) while the temperature is kept below 20° C.

After maintaining the solution at 20° C. for about 60 minutes, the reaction solution is quenched by addition of 500 L of water and 55 Kg of 20% aqueous HCl solution added thereto to adjust to pH 2 to precipitate crystals which are collected by filtration.

The crude crystals are washed with water and subsequently with methanol, and dried to give $N^1$-methoxycarbonyl-$N^4$-[(2-methyl-4-chlorophenoxy)acetyl]sulfanilamide (Compound No. 6; powder, 10.91 Kg, Yield, 78.00%), mp. 184°–185° C.

In a similar manner, the compounds Nos. 2–5, No. 9 and Nos. 19–23 listed in Table 1 above are prepared. The compounds Nos. 7 and 8 are prepared by converting the compound No. 6, on treatment with sodium hydroxide and potassium hydroxide, respectively in water.

SYNTHESIS 2

A mixture of sulfanilamide (87.0 g, 0.5 mole) and 2-methyl-4-chlorophenoxyacetic acid (100.0 g, 0.5 mole) is heated under stirring in an oil bath in vacuo.

The mixture is melted down at 107° C., and crystals appear as a precipitate in the melted mixture and solidify suddenly after heating at 145° C. for about 30 minutes.

The mixture is then suspended in methanol and filtered to give crystals. Recrystallization from acetone affords $N^4$-(2-methyl-4-chlorophenoxy)acetylsulfanilamide (Compound No. 1, powder). 40 g, 22.47%, mp. 218°–220° C.

SYNTHESIS 3

A mixture of 1-(2-methyl-4-chlorophenoxy)propionic acid (4.0 g, 0.018 mole) with thionyl chloride (4.4 g, 0.037 mole) is refluxed at 90°–110° C. for about 3 hours and subsequently allowed to stand overnight.

The reaction mixture is then evaporated in vacuo to remove the excess of thionyl chloride and a solution of $N^1$-methoxycarbonylsulfanilamide (4.0 g, 0.032 mole) in pyridine (26.0 ml) is dropwise added thereto while being maintained at 15°–20° C. for about 3 minutes.

After stirring at 20°–30° C. for about 1.5 hours, the mixture is quenched with a mixture of 35% hydrochloric acid (31.6 g) and water (32 ml)(adjusted at pH 2.0).

Oily material separated in the adjusted mixture is recovered from the supernatant by decantation, dissolved into an aqueous solution of sodium hydroxide, and then precipitated again with 20% hydrochloric acid to give crude crystals.

Recrystallization of the crude crystals from benzene affords $N^1$-methoxycarbonyl-$N^4$-[1-(2-methyl-4-chlorophenoxy)propionyl]sulfanilamide (Compound No. 17, powder). 5.7 g, 71.6%, mp. 86°–87° C.

SYNTHESIS 4

(2-Methyl-4-chlorophenoxy)acetyl chloride (10.98 g, 0.048 mole) is dropwise added to a solution of $N^1$-acetylsulfanilamide (9.64 g, 0.048 mole) in pyridine (95 ml), and this mixture is allowed to react under stirring at 50°–75° C. for about 30 minutes.

After removal of the excess of pyridine under reduced pressure, the mixture is combined with water (100 ml) to give a slurry, which is then adjusted to pH 2.0 by addition of 35% hydrochloric acid to precipitate crude crystals.

The crude crystals recovered from the mixture are combined with a mixture of acetone (300 ml) and water (140 ml), to which a 10% sodium hydroxide aqueous solution is dropwise added to dissolve the crystals.

The solution is treated with a small amount of decoloring charcoal, which is removed by filtration, and is neutralized with 35% hydrochloric acid to precipitate crystals of $N^1$-acetyl-$N^4$-(2-methyl-4-chlorophenoxy)acetylsulfanilamide (Compound No. 18, leaflet). 11.84 g, 60.24%, mp. 253°–255° C.

Formulations:

1. Wettable powder:

A mixture of the following composition is ground and kneaded to give a wettable powder which contains 50% of the active ingredient.

| | |
|---|---|
| Compound of Table 1 | 50 parts. |
| Sorpol (an emulsifier for agrochemicals, available from Toho Chemical Ind. Ltd.) | 5 parts. |
| Lunox (a Stablizing agent, available from Toho Chemical Ind. Ltd.) | 3 parts. |
| Carplex 80 (a fine powdery silica, available from Shionogi & Co., Ltd.) | 15 parts. |
| Kaolin | 27 parts |

2. Granules:

A mixture of the following composition is ground and kneaded with water. The obtained mixture is granulated in a conventional manner and dried to give granules which contain 5% of the active ingredient.

| | |
|---|---|
| Compound of Table 1 | 5 parts. |
| Calcium lignin sulfonate | 5 parts. |
| Bentonite | 30 parts. |
| Clay | 60 parts. |

3. Liquid preparation:

A liquid preparation which contains 10% of the active ingredient is obtained by mixing 10 parts of the compound No. 7 or 8, 5 parts of sorpol and 85 parts of water.

Application experiments:

The pre- and post-emergence applications and their evaluations were performed in the following manner throughout Examples 1 to 5.

(i) Pre-emergence application (the emergence inhibiting activity):

Seeds (25 pieces for respective species) of the plant to be tested are put in a polyethylene cup of 9 cm in diameter filled with sandy loam. After the seeding, the surface of the loam is covered with soil of 5 mm in thickness and an aqueous suspension of the compounds (as an acetone solution, further containing Tween 20 in the amount of 100 ppm) is sprayed with a sprayer over the surface of the covering soil. The amount of the sprayed suspension is adjusted so that the water used for dilution is 10 L per are. The plants are kept in a sun light greenhouse at 25° C.

Evaluations are made 3 weeks after the application and presented by the scores in the 6 degrees (common to the subsequent experiments, except otherwise specified) below.

5: Completely killing or non-emergence.
4: Fatally damaging.
3: Good effect.
2: Fair effect influence.
1: Slight effect.
0: No effect.

(ii) Post-emergence application (the growth inhibiting activity):

Young seedlings 10 days after the seeding were treated with the aqueous solution of the compound (I) to be observed and evaluated 3 weeks after the treatment in the same manner as mentioned in (i) Pre-emergence application.

EXAMPLE 1

Each plant indicated in Table 2 was treated with the compounds assigned as Nos. 1-22 and the reference compounds A-E at the time of seeding and 10 days after the seeding. The plants were observed in the same manner as defined above. The results of the observations are summarized in Table 2 below.

From the results, it is appreciated that all of the compounds of the present invention have the activity inhibiting the emergence of weeds, but no influence on the growth of the same weeds after the emergence.

It is noteworthy that the reference compounds have the moiety as the compounds Nos. 1-22 but show a remarkable difference between both series of compounds.

Table 2 indicates that, in practical application, the compounds of the present invention may be applied before transplanting of the growing crops or during the growth of the crops in controlling only the weeds which would emerge thereafter.

It also indicates that the compounds of the present invention are active against both of the broad-leaf weeds and gramineous weeds as far as the application is performed before their emergence, whereas some of the reference compounds are effective only on the broad-leaf weeds. Some of the reference compounds act similarly in both pre- and post-emergence application.

TABLE 2

| Compd. No. | Barnyard grass | Crab-grass | Smart-weed | Rape | Slender amaranth |
|---|---|---|---|---|---|
| (Dose: 10g/a) | | | | | |
| Emergence inhibiting activity | | | | | |
| 1 | 1 | 4 | 2 | 4 | 1 |
| 2 | 4 | 5 | 5 | 5 | 1 |
| 3 | 3 | 5 | 4 | 5 | 2 |
| 4 | 3 | 5 | 5 | 5 | 2 |
| 5 | 4 | 5 | 5 | 5 | 4 |
| 6 | 5 | 5 | 5 | 5 | 5 |
| 7 | 5 | 5 | 3 | 5 | 5 |

TABLE 2-continued

| Compd. No. | Barnyard grass | Crab-grass | Smart-weed | Rape | Slender amaranth |
|---|---|---|---|---|---|
| (Dose: 10g/a) | | | | | |
| 8 | 5 | 5 | 5 | 5 | 5 |
| 9 | 5 | 5 | 2 | 5 | 5 |
| 10 | 3 | 5 | 3 | 3 | 2 |
| 11 | 3 | 5 | 2 | 3 | 2 |
| 12 | 5 | 5 | 5 | 5 | 0 |
| 13 | 4 | 5 | 2 | 3 | 2 |
| 14 | 5 | 5 | 2 | 5 | 0 |
| 15 | 4 | 5 | 5 | 5 | 0 |
| 16 | 5 | 5 | 2 | 5 | 0 |
| 17 | 4 | 5 | 0 | 1 | 2 |
| 18 | 0 | 2 | 1 | 2 | 0 |
| 19 | 4 | 5 | 1 | 4 | 0 |
| 20 | 4 | 5 | 3 | 5 | 0 |
| 21 | 0 | 0 | 1 | 3 | 1 |
| 22 | 1 | 4 | 1 | 2 | 0 |
| A* | 5 | 5 | 4 | 5 | 0 |
| B* | 2 | 5 | 3 | 2 | 0 |
| C* | 0 | 0 | 0 | 0 | 0 |
| D* | 0 | 0 | 1 | 1 | 1 |
| E* | 0 | 1 | 0 | 3 | 1 |
| Growth inhibiting activity | | | | | |
| 1 | 0 | 0 | 0 | 0 | 0 |
| 2 | 0 | 0 | 0 | 0 | 0 |
| 3 | 0 | 0 | 0 | 0 | 0 |
| 4 | 0 | 0 | 0 | 0 | 0 |
| 5 | 0 | 0 | 0 | 0 | 0 |
| 6 | 0 | 0 | 0 | 0 | 0 |
| 7 | 1 | 2 | 0 | 0 | 0 |
| 8 | 1 | 0 | 0 | 0 | 0 |
| 9 | 0 | 0 | 0 | 0 | 0 |
| 10 | 0 | 0 | 0 | 0 | 0 |
| 11 | 0 | 0 | 0 | 0 | 0 |
| 12 | 0 | 0 | 0 | 0 | 0 |
| 13 | 0 | 0 | 0 | 0 | 0 |
| 14 | 0 | 0 | 0 | 0 | 0 |
| 15 | 0 | 0 | 0 | 0 | 0 |
| 16 | 0 | 0 | 0 | 0 | 0 |
| 17 | 0 | 0 | 0 | 0 | 0 |
| 18 | 0 | 0 | 0 | 0 | 0 |
| 19 | 0 | 0 | 0 | 0 | 0 |
| 20 | 0 | 0 | 0 | 0 | 0 |
| 21 | 0 | 0 | 0 | 0 | 0 |
| 22 | 0 | 0 | 0 | 0 | 0 |
| A* | 5 | 5 | 5 | 4 | 0 |
| B* | 2 | 5 | 4 | 1 | 0 |
| C* | 0 | 0 | 2 | 5 | 2 |
| D* | 0 | 0 | 5 | 5 | 5 |
| E* | 0 | 0 | 5 | 5 | 5 |

*Reference compounds:
A: $N^1$-methoxycarbonylsulfanilamide.
B: $N^1$-carbamoylsulfanilurea.
C: 4-chlorophenoxyacetic acid.
D: 2,4-dichlorophenoxyacetic acid.
E: 2-methyl-4-chlorophenoxyacetic acid.

EXAMPLE 2

In the same manner as described above in (ii) the post-emergence application, the compounds of the present invention were applied to the useful crops as indicated in Table 3 in order to compare the influence on young seedlings of crops with the effect against the weeds which would emerge thereafter in the absence of the application. The results are summarized in Table 3 below.

As indicated in Table 3, any of the compounds demonstrates a powerful emergence inhibiting or herbicidal activity against main species of weeds, but no influence on the seedlings of corn or soybean was observed.

TABLE 3

(Dose: 10g/a)

| Compd. No. | Weeds | | | Crops | | | | |
|---|---|---|---|---|---|---|---|---|
| | Crab-grass | Barn-yard grass | Smart-weed | Slender ama-ranth | Wheat | Corn | Soy-bean | Cucum-ber | Rape |
| 1 | 4 | 1 | 4 | 2 | 0 | 0 | 0 | 0 | 4 |
| 2 | 5 | 5 | 5 | 1 | 5 | 0 | 0 | 5 | 5 |
| 3 | 5 | 5 | 5 | 3 | 0 | 0 | 0 | 5 | 5 |
| 4 | 5 | 5 | 5 | 1 | 0 | 0 | 0 | 5 | 1 |
| 5 | 5 | 5 | 5 | 4 | 0 | 0 | 0 | 2 | 5 |
| 6 | 5 | 5 | 5 | 5 | 1 | 0 | 1 | 5 | 5 |
| 9 | 5 | 5 | 5 | 5 | 5 | 0 | 0 | 0 | 3 |
| 10 | 5 | 3 | 4 | 3 | 0 | 0 | 1 | 3 | 4 |
| 11 | 3 | 2 | 3 | 1 | 0 | 0 | 0 | 3 | 2 |
| 12 | 5 | 4 | 5 | 0 | 0 | 0 | 0 | 1 | 4 |
| 13 | 5 | 2 | 2 | 0 | 0 | 0 | 0 | 0 | 4 |
| 14 | 5 | 3 | 3 | 0 | 0 | 0 | 0 | 0 | 2 |
| 15 | 5 | 3 | 3 | 0 | 3 | 0 | 0 | 0 | 3 |
| 16 | 5 | 4 | 3 | 0 | 5 | 0 | 0 | 0 | 3 |
| 17 | 3 | 5 | 4 | 4 | 0 | 0 | 0 | 0 | 1 |
| 18 | 4 | 1 | 0 | 4 | 0 | 0 | 0 | 0 | 2 |
| 19 | 5 | 4 | 4 | 0 | 2 | 0 | 0 | 0 | 1 |
| 20 | 4 | 5 | 5 | 0 | 3 | 0 | 0 | 3 | 3 |
| 21 | 1 | 1 | 2 | 1 | 0 | 0 | 0 | 0 | 0 |
| 22 | 4 | 3 | 3 | 1 | 0 | 0 | 0 | 0 | 3 |
| A* | 4 | 5 | 5 | 0 | 5 | 4 | 3 | 5 | 5 |
| B* | 5 | 5 | 5 | 0 | 5 | 5 | 5 | 3 | 5 |
| C* | 0 | 0 | 0 | 0 | 0 | 0 | 0 | 0 | 0 |
| D* | 0 | 0 | 1 | 1 | 0 | 0 | 0 | 1 | 1 |
| E* | 0 | 0 | 0 | 1 | 0 | 0 | 0 | 1 | 1 |

*Reference compounds as noted above.

Of these compounds No. 1, Nos. 3 through 6, Nos. 10 through 14, Nos. 17 and 18, and Nos. 21 and 22 did not affect wheat; Nos. 1 and 9, Nos. 13 through 19, and Nos. 21 and 22 did not affect cucumber; and Nos. 4, 17, 19 and 21 did not affect rape.

In contrast, however, a herbicidal or emergence inhibiting activity is appreciated with the reference compounds A and B but they also demonstrate a considerable adverse influence on any of the tested crops.

The rest of the reference compounds, i.e., C, D and E are inactive against both the weeds and the crops.

EXAMPLE 3

Under the same conditions as described in the preceding examples, the influences of some of the compounds of the present invention were investigated on the useful crops after their transplanting on upland soil in contrast to those of the reference compounds. Each of the evaluated compounds was formulated into a wettable powder (Formulation 1 as disclosed above). The results are summarized in Table 4 below.

As seen from Table 4, it is confirmed that the compounds of the present invention are highly safe to the useful crops in general and that the compounds Nos. 4, 5 and 6 have a unique property suitable for use in post-transplanting treatment. On the other hand, any of the reference compounds gives an irrevocable damage on the useful crops.

TABLE 4

| Compd. No. | Dose g/a | Let-tuce | Onion | Beet | Tabacco | Cab-bage | Cu-cumber |
|---|---|---|---|---|---|---|---|
| 1 | 10 | 0 | 0 | 0 | 0 | 0 | 0 |
| | 30 | 1 | 0 | 0 | 0 | 0 | 0 |
| 2 | 10 | 2 | 0 | 0 | 0 | 0 | 0 |
| | 30 | 5 | 0 | 0 | 1 | 0 | 1 |
| 3 | 10 | 1 | 0 | 0 | 1 | 0 | 0 |
| | 30 | 2 | 2 | 1 | 1 | 4 | 2 |
| 4 | 10 | 0 | 0 | 0 | 0 | 0 | 0 |
| | 30 | 0 | 0 | 1 | 0 | 0 | 0 |
| 5 | 10 | 1 | 0 | 0 | 0 | 0 | 0 |
| | 30 | 1 | 0 | 2 | 1 | 0 | 0 |
| 6 | 5 | 0 | 0 | 0 | 0 | 0 | 0 |
| | 10 | 1 | 0 | 0 | 0 | 0 | 0 |
| | 30 | 2 | 0 | 1 | 0 | 0 | 0 |
| 9 | 10 | 1 | 0 | 0 | 1 | 0 | 0 |
| | 30 | 1 | 0 | 0 | 1 | 1 | 0 |
| A'** | 10 | 5 | 5 | 1 | 5 | 5 | 2 |
| | 30 | 5 | 5 | 2 | 5 | 5 | 5 |
| E* | 10 | 5 | 5 | 5 | 5 | 5 | 5 |
| | 30 | 5 | 5 | 5 | 5 | 5 | 5 |
| D* | 10 | 5 | 5 | 5 | 5 | 5 | 5 |
| | 30 | 5 | 5 | 5 | 5 | 5 | 5 |

**A': $N^1$-methoxycarbonyl-$N^4$-acetylsulfanilamide
*Reference compounds as noted above.

EXAMPLE 4

Test of the post-emergence application was performed under the same conditions as described in Example 1, with the compounds Nos. 2, 3 and 6 and a reference compound F (Linuron: 3-(3,4-dichlorophenyl)-1,1-methoxymethylurea). In this test, the dose-activity relationship, particularly, at lower dose levels, was elucidated as shown in Table 5 below. In Table 5, the herbicidal activity is expressed by percentages (w/w%) of survived weeds in the test field to those in the control field.

TABLE 5

| Compd. No. | Dose g/a | Barnyard grass | Ladysthumb | Chickweed | Nutsedge |
|---|---|---|---|---|---|
| 2 | 2.5 | 80 | 0 | 50 | 20 |
| | 5.0 | 40 | 0 | 20 | 10 |
| | 10.0 | 20 | 0 | 0 | 0 |
| | 15.0 | 0 | 0 | 0 | 0 |
| 3 | 2.5 | 60 | 10 | 40 | 10 |
| | 5.0 | 40 | 0 | 20 | 0 |

TABLE 5-continued

| Compd. No. | Dose g/a | Barnyard grass | Ladysthumb | Chickweed | Nutsedge |
|---|---|---|---|---|---|
| | 10.0 | 0 | 0 | 0 | 0 |
| | 15.0 | 0 | 0 | 0 | 0 |
| 6 | 2.5 | 50 | 0 | 0 | 0 |
| | 5.0 | 30 | 0 | 0 | 0 |
| | 10.0 | 0 | 0 | 0 | 0 |
| | 15.0 | 0 | 0 | 0 | 0 |
| F* | 2.5 | 100 | 100 | 100 | 100 |
| | 5.0 | 100 | 100 | 100 | 100 |
| | 10.0 | 100 | 80 | 70 | 80 |
| | 15.0 | 80 | 40 | 50 | 70 |

*Reference compound: Linuron

The compounds Nos. 2, 3 and 6 each demonstrate a satisfactory herbicidal activity against ladysthumb and nutsedge even at a low dose of 2.5 g/a, that against chickweed at a dose of 5.0 g/a, and that against all of the tested weeds at a dose of 10.0 g/a.

EXAMPLE 5

Under the same conditions as described in Examples 1 and 2, the compounds of the present invention were applied to the useful crops in order to investigate the effect of the pre-emergence and post-emergence applications. The results are summarized in Table 6 below.

As indicated in Table 6, it is confirmed that all of the compounds evaluated here have no adverse effect on all of the crops in the post-emergence application. However, the compounds Nos. 10 and 17 give some influences on some crops in pre-emergence application.

TABLE 6

| Compd. No. | Dose g/a | Pre-emergence treatment | | | | | Post-emergence treatment | | | | |
|---|---|---|---|---|---|---|---|---|---|---|---|
| | | Corn | Sorghum | Wheat | Soybean | Beet | Corn | Sorghum | Wheat | Soybean | Beet |
| 2 | 10 | 0 | 0 | 0 | 0 | 0 | 0 | 0 | 0 | 0 | 0 |
| | 20 | 0 | 0 | 0 | 0 | 0 | 0 | 0 | 0 | 0 | 0 |
| 3 | 10 | 0 | 0 | 0 | 0 | 0 | 0 | 0 | 0 | 0 | 0 |
| | 20 | 0 | 0 | 0 | 0 | 0 | 0 | 0 | 0 | 0 | 0 |
| 4 | 10 | 0 | 0 | 1 | 0 | 2 | 0 | 0 | 0 | 0 | 0 |
| | 20 | 0 | 0 | 1 | 0 | 3 | 0 | 0 | 0 | 0 | 0 |
| 10 | 10 | 0 | 2 | 3 | 0 | 3 | 0 | 0 | 0 | 0 | 0 |
| | 20 | 0 | 3 | 4 | 0 | 5 | 0 | 0 | 0 | 0 | 0 |
| 12 | 10 | 0 | 0 | 2 | 1 | 0 | 0 | 0 | 0 | 0 | 0 |
| | 20 | 0 | 0 | 3 | 1 | 0 | 0 | 0 | 0 | 0 | 0 |
| 14 | 10 | 0 | 1 | 0 | 0 | 0 | 0 | 0 | 0 | 0 | 0 |
| | 20 | 0 | 2 | 0 | 0 | 0 | 0 | 0 | 0 | 0 | 0 |
| 17 | 10 | 2 | 3 | 2 | 0 | 5 | 0 | 0 | 0 | 0 | 0 |
| | 20 | 4 | 3 | 4 | 0 | 5 | 0 | 0 | 0 | 0 | 0 |
| 19 | 10 | 0 | 1 | 2 | 0 | 0 | 0 | 0 | 0 | 0 | 0 |
| | 20 | 0 | 2 | 2 | 0 | 0 | 0 | 0 | 0 | 0 | 0 |
| 20 | 10 | 0 | 1 | 3 | 0 | 2 | 0 | 0 | 0 | 0 | 0 |
| | 20 | 0 | 2 | 3 | 0 | 3 | 0 | 0 | 0 | 0 | 0 |
| F* | 10 | 0 | 1 | 1 | 1 | 3 | 1 | 2 | 2 | 3 | 3 |
| | 20 | 1 | 3 | 2 | 2 | 3 | 2 | 2 | 3 | 4 | 4 |

*Reference compound as noted.

In the pre-emergence application, it is found that most of the compounds except No. 17 are safe for corn, and those except No. 12 are safe for soybean, and those except Nos. 4, 10 and 17 are safe for beet. Furthermore, the compounds Nos. 2, 3, 4, and 10 are safe for sorghum while the compounds Nos. 2, 3 and 14 are safe for wheat.

In contrast to these, the reference compound F, Linuron, inhibits the emergence and growth of all of the tested crops except in the case of the pre-emergence application on corn.

EXAMPLE 6

(iii) Soil incorporation experiment

A butt of 40×40 cm was filled with sandy loam wherein the compounds in the specified dose indicated in Table 7 were incorporated in the loam so that the compounds were evenly distributed throughout the layer at a depth of 5 cm. The seeds of the plants to be tested were placed therein (in the case of perennial ones, their tubers are transplanted). The experiment was performed under the same conditions as described above and the results of the observation are summarized in Table 7 below.

TABLE 7A

| Compd. No. | Dose g/a | Barnyard grass | Crab-grass | Smart-weed | Slender amaranth | Purple nutsedge | Mug wort | Field horsetail | Bind-weed | Corn | Wheat | Soybean |
|---|---|---|---|---|---|---|---|---|---|---|---|---|
| 3 | 5 | 5 | 5 | 5 | 1 | 0 | 5 | 5 | 5 | 0 | 0 | 0 |
| | 10 | 5 | 5 | 5 | 3 | 0 | 5 | 5 | 5 | 0 | 0 | 2 |
| | 20 | 5 | 5 | 5 | 5 | 2 | 5 | 5 | 5 | 0 | 1 | 1 |
| 4 | 5 | 5 | 5 | 5 | 0 | 0 | 0 | 0 | 0 | 0 | 0 | 0 |
| | 10 | 5 | 5 | 5 | 1 | 0 | 0 | 0 | 1 | 0 | 0 | 2 |
| | 20 | 5 | 5 | 5 | 2 | 0 | 1 | 1 | 2 | 0 | 0 | 2 |
| 5 | 5 | 5 | 5 | 5 | 3 | 0 | 1 | 1 | 1 | 0 | 0 | 0 |
| | 10 | 5 | 5 | 5 | 5 | 0 | 3 | 2 | 2 | 0 | 0 | 0 |
| | 20 | 5 | 5 | 5 | 5 | 2 | 4 | 3 | 5 | 0 | 0 | 1 |
| 6 | 5 | 5 | 5 | 5 | 5 | 0 | 2 | 5 | 5 | 0 | 0 | 0 |
| | 10 | 5 | 5 | 5 | 5 | 2 | 5 | 5 | 5 | 0 | 1 | 0 |
| | 20 | 5 | 5 | 5 | 5 | 3 | 5 | 5 | 5 | 0 | 5 | 1 |
| 10 | 5 | 2 | 5 | 3 | 2 | 1 | 1 | 2 | 3 | 0 | 2 | 0 |
| | 10 | 3 | 5 | 3 | 2 | 2 | 2 | 2 | 3 | 0 | 2 | 0 |
| | 30 | 5 | 5 | 5 | 3 | 3 | 4 | 4 | 5 | 0 | 4 | 1 |
| 12 | 5 | 3 | 5 | 5 | 0 | 0 | 4 | 3 | 3 | 0 | 0 | 0 |
| | 10 | 5 | 5 | 5 | 0 | 1 | 5 | 3 | 3 | 0 | 1 | 0 |
| | 30 | 5 | 5 | 5 | 0 | 2 | 5 | 4 | 5 | 0 | 2 | 0 |

TABLE 7A-continued

| Compd. No. | Dose g/a | Barnyard grass | Crab- grass | Smart- weed | Slender amaranth | Purple nutsedge | Mug wort | Field horsetail | Bind- weed | Corn | Wheat | Soy- bean |
| --- | --- | --- | --- | --- | --- | --- | --- | --- | --- | --- | --- | --- |
| 14 | 5 | 3 | 5 | 5 | 0 | 1 | 2 | 5 | 3 | 0 | 0 | 0 |
|  | 10 | 5 | 5 | 5 | 0 | 2 | 2 | 5 | 4 | 0 | 0 | 0 |
|  | 30 | 5 | 5 | 5 | 0 | 3 | 4 | 5 | 5 | 0 | 0 | 0 |

TABLE 7B

| Compd. No. | 17 | | | 19 | | | 20 | | | 22 | | |
| --- | --- | --- | --- | --- | --- | --- | --- | --- | --- | --- | --- | --- |
| Dose | 5 | 10 | 30 | 5 | 10 | 30 | 5 | 10 | 30 | 5 | 10 | 30 |
| Barnyard grass | 3 | 2 | 3 | 3 | 4 | 4 | 4 | 5 | 5 | 2 | 3 | 4 |
| Crabgrass | 5 | 5 | 5 | 5 | 5 | 5 | 5 | 5 | 5 | 5 | 5 | 5 |
| Smartweed | 3 | 3 | 4 | 2 | 3 | 4 | 4 | 5 | 5 | 2 | 2 | 3 |
| Slender amaranth | 3 | 4 | 5 | 0 | 0 | 0 | 0 | 0 | 0 | 0 | 0 | 1 |
| Corn | 0 | 2 | 4 | 0 | 0 | 0 | 0 | 0 | 0 | 0 | 0 | 0 |
| Wheat | 0 | 1 | 4 | 0 | 0 | 2 | 0 | 1 | 3 | 0 | 0 | 0 |
| Soybean | 0 | 0 | 1 | 0 | 0 | 0 | 0 | 0 | 0 | 0 | 0 | 0 |
| Tomato | 1 | 2 | 4 | 0 | 1 | 2 | 0 | 0 | 2 | 0 | 0 | 0 |
| Cucumber | 2 | 3 | 5 | 0 | 2 | 3 | 0 | 3 | 5 | 0 | 0 | 0 |

From what has been indicated by Table 7, it is confirmed that a higher herbicidal activity can reasonably be expected with each of the evaluated compounds even at its lower dosage levels when they are used in the soil incorporation than that obtained with the same compound in the surface application, and that the activity is not limited only to annual weeds but also to perennial weeds by virtue of the extended depth of treatment.

In addition, it is also found that each of the evaluated compounds is capable of maintaining its distinguishing selectivity in herbicidal activity between the useful crops and weeds.

In terms of the spectrum of weed-killing, the compounds Nos. 4, 10, 12 and 14 are shown to kill barnyard grass, crabgrass and smartweed but have only weak herbicidal activities against slender amaranth and perennial weeds. The compound No. 5 kills all of the annual weeds at doses above 10 g/a but kills only bindweed of the perennial weeds.

The compounds Nos. 3 and 6 kill most of the tested annual and perennial weeds except for purple nutsedge.

The other evaluated compounds demonstrate considerable herbicidal activities against most of the tested annual weeds except for slender amaranth and the perennial weeds except for purple nutsedge.

As regards adverse influences on the useful crops, most of the evaluated compounds exhibit no or only a slight adverse influence on corn.

Compounds Nos. 3, 4, 5, 12, 14, 19 and 22 exhibit no or only a slight adverse influence on wheat. Compound No. 22 exhibits no influence on either tomato or cucumber.

As described above, the compound No. 6 is found to be useful for corn and soybean, and compounds Nos. 3 and 4 are useful for corn and wheat. The compounds Nos. 17~22 are acceptable for corn and soybean in some instances.

EXAMPLE 7

(iv) Rice seedling test (pot):
Pre-transplanting treatment
In a Wagner pot of 1/5,000 are, filled with paddy soil and water, and treated with a specified amount of the compounds to be evaluated, seeds of weeds were placed and two rice plants were planted.

The plants were kept and observed in the same manner as described in (i)–(iii) above.

One month after the treatment, the plants were collected and weighed in order to calculate the rate of survivors. The results are summarized in Table 8 below. The rate of the survivors was calculated and expressed as a percentage of the weight of the treated plants of those in the control field.

TABLE 8

| | | Rate of survived weeds (%) | | | Rate of survived rice (%) | |
| --- | --- | --- | --- | --- | --- | --- |
| Compd. No. | Dose g/a | Barnyard grass | Small flower umbrella plant | Broad-leaf weeds | Length | Stem |
| 2 | 1.0 | 60 | 30 | 20 | 100 | 95 |
|  | 2.0 | 30 | 20 | 20 | 95 | 90 |
|  | 5.0 | 0 | 10 | 0 | 90 | 86 |
| 3 | 1.0 | 70 | 40 | 40 | 100 | 100 |
|  | 2.0 | 60 | 0 | 0 | 95 | 100 |
|  | 5.0 | 20 | 0 | 0 | 100 | 95 |
| 5 | 1.0 | 80 | 0 | 20 | 100 | 100 |
|  | 2.0 | 0 | 0 | 0 | 100 | 100 |
| 6 | 1.0 | 0 | 0 | 0 | 95 | 90 |
|  | 2.0 | 0 | 0 | 0 | 85 | 70 |
| 7 | 1.0 | 20 | 0 | 0 | 100 | 100 |
|  | 2.0 | 5 | 0 | 0 | 100 | 100 |
|  | 5.0 | 0 | 0 | 0 | 100 | 95 |
| 8 | 1.0 | 15 | 0 | 10 | 100 | 100 |
|  | 2.0 | 0 | 0 | 0 | 100 | 100 |
| 9 | 1.0 | 0 | 0 | 0 | 100 | 100 |
|  | 2.0 | 0 | 0 | 0 | 100 | 100 |
|  | 5.0 | 0 | 0 | 0 | 100 | 100 |
| 10 | 1.0 | 10 | 30 | 0 | 95 | 100 |
|  | 5.0 | 0 | 10 | 0 | 95 | 90 |
|  | 10.0 | 0 | 0 | 0 | 85 | 80 |
| 11 | 1.0 | 50 | 10 | 20 | 98 | 100 |
|  | 5.0 | 40 | 0 | 0 | 90 | 95 |
|  | 10.0 | 20 | 0 | 0 | 80 | 90 |
| 12 | 1.0 | 90 | 50 | 20 | 100 | 100 |
|  | 5.0 | 80 | 20 | 20 | 100 | 100 |
|  | 10.0 | 0 | 0 | 0 | 100 | 100 |
| 13 | 1.0 | 95 | 20 | 0 | 100 | 100 |
|  | 5.0 | 80 | 20 | 0 | 100 | 100 |
|  | 10.0 | 0 | 0 | 0 | 100 | 100 |
| 14 | 1.0 | 70 | 60 | 15 | 100 | 100 |
|  | 5.0 | 40 | 40 | 0 | 100 | 100 |
|  | 10.0 | 40 | 40 | 0 | 100 | 100 |
| 15 | 1.0 | 85 | 20 | 35 | 100 | 100 |
|  | 5.0 | 80 | 20 | 20 | 100 | 95 |
|  | 10.0 | 20 | 0 | 0 | 90 | 90 |
| 16 | 1.0 | 90 | 85 | 10 | 100 | 100 |
|  | 5.0 | 90 | 80 | 0 | 100 | 95 |
|  | 10.0 | 20 | 0 | 0 | 95 | 90 |
| 17 | 1.0 | 15 | 35 | 15 | 100 | 95 |
|  | 5.0 | 0 | 0 | 0 | 95 | 90 |
|  | 10.0 | 0 | 0 | 0 | 80 | 85 |
| 19 | 1.0 | 85 | 25 | 20 | 100 | 100 |
|  | 5.0 | 75 | 0 | 0 | 100 | 100 |
|  | 10.0 | 0 | 0 | 0 | 95 | 95 |
| 20 | 1.0 | 65 | 15 | 15 | 100 | 102 |
|  | 5.0 | 55 | 0 | 0 | 100 | 100 |
|  | 10.0 | 0 | 0 | 0 | 100 | 100 |
| 21 | 1.0 | 75 | 35 | 25 | 105 | 100 |
|  | 5.0 | 65 | 15 | 0 | 100 | 100 |
|  | 10.0 | 15 | 0 | 0 | 100 | 95 |
| 22 | 1.0 | 80 | 90 | 35 | 100 | 105 |
|  | 5.0 | 75 | 85 | 20 | 100 | 102 |

TABLE 8-continued

| Compd. No. | Dose g/a | Barnyard grass | Small flower umbrella plant | Broad-leaf weeds | Rate of survived rice (%) Length | Rate of survived rice (%) Stem |
|---|---|---|---|---|---|---|
| | 10.0 | 65 | 55 | 15 | 100 | 100 |

As is apparent from Table 8 above, it is confirmed that the compounds Nos. 6 and 9 completely inhibit the emergence of barnyard grass, small flower umbrella plants and other broad-leaf weeds at a dose of 1.0 g/a, and that the compounds Nos. 6, 7 and 8, the alkali metal salts of compound No. 6, and the compound No. 17 similarly have high herbicidal activities.

As regards safety for rice plant, a tendency of inhibiting the growth is appreciated to some extent in the compounds Nos. 6 and 17 but none with the compounds Nos. 7, 8 and 9.

EXAMPLE 8

(v) Rice seedling test (field):
Pre-transplanting treatment

Concrete pots of $50 \times 50 \times 50$ cm$^3$, placed in an outdoor field, were filled with paddy soil (sandy loam) and water, and treated with the compounds as mentioned in Table 9 at pre-fixed doses. Three days after the treatment, two plants of rice were planted in each pot.

The pots were kept under natural daylight at temperatures ranging from 17° C. to 28° C. for 50 days. Then, the rice plants and weeds are totally pulled out and weighed. The results are summarized in Table 9. The rate of survivors was calculated in the same manner as in Example 7.

cept for barnyard grass at the respective dosage levels. The compound No. 5 inhibits the emergences of most of the tested weeds except for barnyard grass and spike flowered rotala.

All of the evaluated compounds are found to have no significant adverse influence on rice.

The reference compound G, which has widely been used as a herbicidal composition for paddy lands in Japan, shows no herbicidal activity against long-stemmed waterwort, while each of the evaluated compounds exhibits an excellent activity against the same weed.

It is further appreciated that the compounds Nos. 9, 10, 17 and 20 are found to have excellent activities against annual weeds in paddy fields with no significant adverse influence on the rice plant.

EXAMPLE 9

(v) Rice seedling test (pot):
Growth inhibiting activity against annual weeds by post-emergence application In a Wagner pot of 1/2,000 are, filled with paddy soil, were placed seeds of annual weeds and two transplanted plants of rice (2.5 leaf-stage LS) per pot, and then flooded.

When the rice and weeds had grown to reach the respective leaf-stage noted below, the sample pot was treated with a pre-fixed amount of an aqueous suspension of the compounds as mentioned in Table 10.

| Rice: | 3.5 LS |
|---|---|
| Barnyard grass: | 2 LS (5 cm) |
| Broad-leaf weeds: | 5 mm |

TABLE 9

| Compound Number | 1 | 5 | 6 | 9 | 10 | 12 | 14 | 17 | 19 | 20 | 22 | G* | H* | I* |
|---|---|---|---|---|---|---|---|---|---|---|---|---|---|---|
| Dose, gram per are | 5.0 | 2.5 | 1.0 | 2.5 | 2.5 | 5.0 | 5.0 | 2.5 | 5.0 | 5.0 | 5.0 | 300 | 300 | 300 |
| Weeds: | | | | | | | | | | | | | | |
| Barnyard grass | 20 | 15 | 15 | 10 | 0 | 15 | 20 | 0 | 25 | 0 | 15 | 5 | 0 | 0 |
| Monochora | 3 | 0 | 0 | 0 | 0 | 0 | 0 | 0 | 0 | 0 | 0 | 0 | 0 | 0 |
| Spike flowered rotala | 20 | 10 | 0 | 0 | 0 | 0 | 0 | 0 | 0 | 0 | 0 | 0 | 0 | 0 |
| Longstemmed waterwort | 10 | 0 | 0 | 0 | 0 | 0 | 0 | 0 | 0 | 0 | 0 | 100 | 0 | 0 |
| Vandella spp. | 0 | 0 | 0 | 0 | 0 | 0 | 0 | 0 | 0 | 0 | 0 | 0 | 0 | 0 |
| Smartweed | 0 | 0 | 0 | 0 | 0 | 0 | 0 | 0 | 0 | 0 | 0 | 0 | 0 | 0 |
| Small flower umbrella plant | 0 | 0 | 0 | 0 | 0 | 0 | 0 | 0 | 0 | 0 | 0 | 0 | 0 | 0 |
| Mat rush | 0 | 0 | 0 | 0 | 0 | 0 | 0 | 0 | 0 | 0 | 0 | 0 | 0 | 0 |
| Rice: | | | | | | | | | | | | | | |
| Length | 90 | 97 | 85 | 100 | 95 | 97 | 95 | 95 | 105 | 100 | 105 | 103 | 95 | 100 |
| Stem | 105 | 91 | 90 | 106 | 90 | 100 | 85 | 97 | 95 | 98 | 100 | 107 | 100 | 97 |
| Wet weight | 95 | 101 | 92 | 109 | 90 | 99 | 99 | 95 | 100 | 103 | 95 | 93 | 97 | 95 |

*Reference compounds:
G: Preparation containing 7% of bentiocarb and 1.5% of simetryne (Trade name: Saturn S, available from Kumiai Chem. Ind. Ltd.).
H: Preparation containing 8% of molinate, 1.5% of simetryne and 0.8% of 2-methyl-4-chlorophenoxyacetic acid (MCP) (Trade name: Yashima mammet SM, available from Yashima Chem. Ind. Ltd.).
I: Preparation containing 7% of 2,4,6-trichlorophenyl-4-nitrophenyl (CNP) (Trade name: M O Granule, available from Mitsui Toatsu Chem. Ind. Ltd.).

From what has been indicated by Table 10, it is confirmed that the compounds Nos. 10, 17 and 20 completely inhibit the emergences of all of the tested weeds at dosage levels as low as 2.5 g/a and 5.0 g/a, respectively. The compounds Nos. 6, 9, 12, 14, 19 and 22 inhibit the emergences of most of the tested weeds ex- The sample pot was controlled in the same manner as described in (i)-(iii) above, and the activities against weeds and influences on rice were observed 45 days after the application. The results expressed in the 6-degree score are summarized in Table 10 below.

TABLE 10

| Compd. No. | Dose g/a | Barnyard grass | Monochoria | Spike-flowered rotala | Vandellia spp. | Long-stemmed waterwort | Smartweed | Nutsedge | Rice |
|---|---|---|---|---|---|---|---|---|---|
| 1 | 2.5 | 2 | 5 | 3 | 5 | 2 | 0 | 2 | 0 |
|   | 5.0 | 2 | 5 | 4 | 5 | 5 | 5 | 5 | 1 |
| 5 | 2.5 | 0 | 5 | 4 | 4 | 5 | 1 | 2 | 0 |
|   | 5.0 | 2 | 5 | 5 | 5 | 5 | 5 | 5 | 0 |
| 7 | 2.5 | 2 | 5 | 5 | 5 | 5 | 5 | 5 | 0 |
|   | 5.0 | 3 | 5 | 5 | 5 | 5 | 5 | 5 | 0 |
| 8 | 2.5 | 0 | 0 | 0 | 1 | 4 | 4 | 4 | 0 |
|   | 5.0 | 2 | 0 | 5 | 5 | 5 | 5 | 5 | 0 |
| 9 | 2.5 | 3 | 5 | 2 | 5 | 5 | 5 | 2 | 0 |
|   | 5.0 | 3 | 5 | 5 | 5 | 5 | 5 | 5 | 0 |
| 10 | 2.5 | 1 | 3 | 3 | 2 | 3 | 3 | 3 | 0 |
|   | 5.0 | 2 | 4 | 4 | 4 | 3 | 4 | 4 | 1 |
|   | 10.0 | 2 | 4 | 4 | 5 | 3 | 4 | 5 | 2 |
| 12 | 2.5 | 0 | 1 | 2 | 1 | 0 | 2 | 1 | 0 |
|   | 5.0 | 0 | 2 | 2 | 2 | 1 | 2 | 2 | 1 |
|   | 10.0 | 0 | 2 | 3 | 3 | 2 | 3 | 3 | 1 |
| 14 | 2.5 | 0 | 2 | 1 | 2 | 1 | 2 | 1 | 0 |
|   | 5.0 | 0 | 2 | 1 | 2 | 1 | 2 | 2 | 1 |
|   | 10.0 | 0 | 2 | 2 | 2 | 2 | 3 | 2 | 1 |
| G* | 300 | 5 | 5 | 5 | 5 | 0 | 5 | 5 | 0 |
| A"* | 50 | 0 | 0 | 0 | 0 | 0 | 0 | 0 | 0 |
|   | 100 | 0 | 0 | 1 | 0 | 0 | 0 | 0 | 0 |
| E'* | 15 | 0 | 1 | 1 | 1 | 1 | 1 | 0 | 0 |
|   | 30 | 1 | 2 | 3 | 2 | 2 | 2 | 2 | 0 |

*Reference compounds:
G: As noted above.
A": Preparation containing 37% of N'-methoxycarbonylsulfanilamide sodium (A) (expressed in ml).
E': Preparation containing 19.5% of MCP (E) sodium.

From Table 10, it is found that the compounds Nos. 1, 5, 7, 8 and 10 each exhibit a herbicidal activity as high as that of the reference compound G against the weeds with some exception of the particular compound on some species of weeds.

No significant adverse influence on rice was observed.

On the other hand, neither of the reference compounds A" and E' is found to have practically satisfactory herbicidal activity against any species of weeds.

The results indicate that each of the evaluated compounds, all being active against annual weeds of a certain leaf-stage, even after their emergence as far as the land is flooded, are useful as herbicides for application in paddy fields.

EXAMPLE 10

(vi) Rice seedling test (pot):

Growth inhibiting activity against perennial weeds by post-emergence application In a Wagner pot of 1/5,000 filled with paddy soil, tubers of perennial weeds were placed, and two plants of rice per pot were transplanted, and then flooded.

When the rice and weeds had grown to reach the respective leaf-stage (LS) noted below, the sample pot was treated with the pre-fixed amounts of an aqueous suspension of the compounds indicated in Table 11.

| Rice: | 3.7 LS |
|---|---|
| Japanese ribbon wapoto: | 3 LS |
| Arrowhead: | 5 LS |
| Bog pond weed: | 2 LS |
| Water nutgrass: | 3 LS |
| Slender spikerush: | 5 nodes (runner) |
| Water chestnut: | 5 LS |

The sample pot was controlled in the same manner as described in (i)–(iii) above and the activities against weeds and influences on rice were observed one month after the application. The results are summarized in Table 11 below.

TABLE 11

| Compd. No. | Dose g/a | Japanese ribbon wapoto | Arrow head | Bog pond weed | Water nutgrass | Slender spikerush | Water chestnut | Rice |
|---|---|---|---|---|---|---|---|---|
| 2 | 5 | 0 | 0 | 5 | 0 | 0 | 2 | 0 |
|   | 20 | 0 | 0 | 5 | 0 | 0 | 2 | 0 |
| 3 | 5 | 0 | 0 | 5 | 1 | 0 | 0 | 0 |
|   | 20 | 3 | 0 | 5 | 5 | 3 | 3 | 0 |
| 4 | 5 | 0 | 0 | 5 | 0 | 0 | 0 | 0 |
|   | 20 | 0 | 0 | 5 | 0 | 0 | 0 | 0 |
| 5 | 5 | 3 | 0 | 5 | 2 | 0 | 0 | 0 |
|   | 20 | 5 | 5 | 5 | 5 | 5 | 3 | 0 |
| 6 | 5 | 5 | 5 | 5 | 5 | 3 | 0 | 0 |
|   | 20 | 5 | 5 | 5 | 5 | 5 | 5 | 1 |
| 7 | 5 | 4 | 4 | 5 | 3 | 0 | 0 | 0 |
|   | 20 | 5 | 5 | 5 | 5 | 5 | 3 | 0 |
| 8 | 5 | 5 | 4 | 5 | 4 | 4 | 0 | 0 |
|   | 20 | 5 | 5 | 5 | 5 | 5 | 5 | 0 |
| 9 | 5 | 3 | 5 | 5 | 3 | 0 | 0 | 0 |
|   | 20 | 5 | 5 | 5 | 5 | 5 | 0 | 0 |
| 10 | 5 | 2 | 4 | 4 | 2 | 3 | 1 | 1 |
|   | 20 | 4 | 5 | 4 | 2 | 5 | 1 | 2 |
| H* | 300 | 4 | 5 | 5 | 5 | 5 | 3 | 0 |
| A" | 100 | 0 | 0 | 0 | 0 | 0 | 0 | 0 |
| E' | 30 | 2 | 3 | 5 | 3 | 2 | 2 | 1 |

From what has been indicated by Table 11, it is found that the compounds Nos. 5, 6, 7 and 8 demonstrate herbicidal activities as high as that of the reference compound H against the six tough species of the growing perennial weeds in paddy soil. Furthermore, each of the compounds Nos. 2, 3 and 4 exhibits a distinguished activity against bog pond weed, the compound No. 9 has an excellent activity against most of the tested weeds except for water chestnut, and the compound No. 10 has excellent activities against arrowhead and slender spikerush.

On the other hand, the reference compounds A″ and E′ have no or only a slight effect on the tested species of the weeds.

In either case of the evaluated compounds including the reference ones, no significant adverse influence on rice was appreciated in the range of the stated dosage level.

From the above results, it is confirmed that the compounds of the present invention are acceptable as a herbicide for paddy fields. Particularly, the compounds Nos. 5, 7 and 8 are useful for removing perennial weeds of certain leaf-stage by post-emergence application, and the other compounds are also acceptable as herbicides for some species of weeds in a flooded paddy field.

What is claimed is:

1. $N^4$-Phenoxyalkanoylsulfanilamides of the formula:

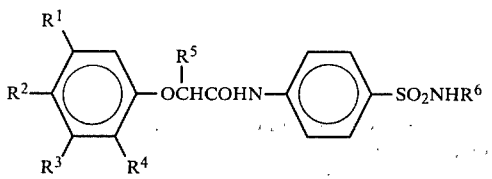

wherein $R^1$, $R^2$, $R^3$, and $R^4$ each independently represents hydrogen, halogen, nitro or lower alkyl, $R^5$ represents hydrogen or lower alkyl and $R^6$ represents hydrogen, lower alkoxycarbonyl, lower alkanoyl or carbamoyl, provided that when $R^1$, $R^3$, $R^4$, and $R^5$ are H and $R^2$ is H or Cl, $R^6$ is not acetyl or hydrogen, or alkali metal, alkaline earth metal or ammonium salts thereof.

2. $N^4$-[(2-Methyl-4-chlorophenoxy)acetyl]sulfanilamide, in accordance with claim 1.

3. $N^1$-Acetyl-$N^4$-[(2-methyl-4-chlorophenoxy)acetyl]-sulfanilamide, in accordance with claim 1.

4. $N^1$-Carbamoyl-$N^4$-[(2-methyl-4-chlorophenoxy)acetyl]-sulfanilamide, in accordance with claim 1.

5. $N'$-Methoxycarbonyl-$N^4$-phenoxyalkanoylsulfanilamides, in accordance with claim 1, of the formula:

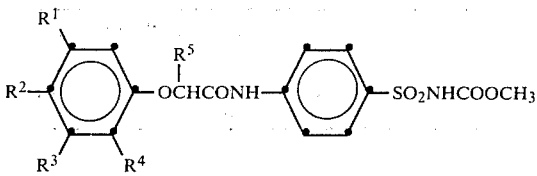

wherein $R^1$, $R^2$, $R^3$, $R^4$ and $R^5$ each has the same significance as defined in claim 1, or sodium, potassium or ammonium salts thereof.

6. $N^1$-Methoxycarbonyl-$N^4$-phenoxyacetylsulfanilamide, in accordance with claim 5.

7. $N^1$-Methoxycarbonyl-$N^4$-[(4-chlorophenoxy)acetyl]sulfanilamide, in accordance with claim 5.

8. $N^1$-Methoxycarbonyl-$N^4$-[(4-fluorophenoxy)acetyl]sulfanilamide, in accordance with claim 5.

9. $N^1$-Methoxycarbonyl-$N^4$-[(4-bromophenoxy)acetyl]sulfanilamide, in accordance with claim 5.

10. $N^1$-Methoxycarbonyl-$N^4$-[(3-chlorophenoxy)acetyl]sulfanilamide, in accordance with claim 5.

11. $N^1$-Methoxycarbonyl-$N^4$-[(2-chlorophenoxy)acetyl]sulfanilamide, in accordance with claim 5.

12. $N^1$-Methoxycarbonyl-$N^4$-[(2-methylphenoxy)acetyl]sulfanilamide, in accordance with claim 5.

13. $N^1$-Methoxycarbonyl-$N^4$-[(3-methylphenoxy)acetyl]sulfanilamide, in accordance with claim 5.

14. $N^1$-Methoxycarbonyl-$N^4$-[(4-methylphenoxy)acetyl]sulfanilamide, in accordance with claim 5.

15. $N^1$-Methoxycarbonyl-$N^4$-[(2-nitrophenoxy)acetyl]sulfanilamide, in accordance with claim 5.

16. $N^1$-Methoxycarbonyl-$N^4$-[(3-nitrophenoxy)acetyl]sulfanilamide, in accordance with claim 5.

17. $N^1$-Methoxycarbonyl-$N^4$-[(2,4-dichlorophenoxy)acetyl]sulfanilamide, in accordance with claim 5.

18. $N^1$-Methoxycarbonyl-$N^4$-[(3,4-dichlorophenoxy)acetyl]sulfanilamide, in accordance with claim 5.

19. $N^1$-Methoxycarbonyl-$N^4$-[(3,5-dichlorophenoxy)acetyl]sulfanilamide, in accordance with claim 5.

20. $N^1$-Methoxycarbonyl-$N^4$-[(3,5-dimethylphenoxy)acetyl]sulfanilamide, in accordance with claim 5.

21. $N^1$-Methoxycarbonyl-$N^4$-[(2,4-dinitrophenoxy)acetyl]sulfanilamide, in accordance with claim 5.

22. $N^1$-Methoxycarbonyl-$N^4$-[(2-methyl-4-chlorophenoxy)acetyl]sulfanilamide, in accordance with claim 5.

23. $N^1$-Methoxycarbonyl-$N^4$-[1-(2-methyl-4-chlorophenoxy)propionyl]sulfanilamide, in accordance with claim 5.

24. A herbicidal composition containing an effective herbicidal amount of at least one of the compounds defined in claim 1 and at least one inert diluent, carrier and/or adjuvant.

* * * * *